United States Patent
Pande et al.

(10) Patent No.: US 10,729,381 B2
(45) Date of Patent: Aug. 4, 2020

(54) PHOTOPLETHYSMOGRAM WITH MOTION ARTIFACT COMPENSATION

(71) Applicant: Texas Instruments Incorporated, Dallas, TX (US)

(72) Inventors: Tarkesh Pande, Richardson, TX (US); David Patrick Magee, Allen, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 344 days.

(21) Appl. No.: 15/192,456

(22) Filed: Jun. 24, 2016

(65) Prior Publication Data

US 2017/0367657 A1 Dec. 28, 2017

(51) Int. Cl.
*A61B 5/00* (2006.01)
*A61B 5/024* (2006.01)

(52) U.S. Cl.
CPC .......... *A61B 5/721* (2013.01); *A61B 5/02416* (2013.01); *A61B 5/6843* (2013.01); *A61B 5/725* (2013.01); *A61B 5/7257* (2013.01); *A61B 2562/0219* (2013.01)

(58) Field of Classification Search
CPC ... A61B 5/721; A61B 5/6843; A61B 5/02416; A61B 5/725
See application file for complete search history.

(56) References Cited

U.S. PATENT DOCUMENTS

| | | |
|---|---|---|
| 3,972,320 A | 8/1976 | Kalman |
| 4,312,358 A | 1/1982 | Barney |
| 5,316,008 A | 5/1994 | Suga et al. |
| 5,865,755 A | 2/1999 | Golub |
| 6,599,251 B2 | 7/2003 | Chen et al. |
| 6,723,054 B1 | 4/2004 | Baruch et al. |
| 7,993,275 B2 | 8/2011 | Banet et al. |
| 2008/0097633 A1 | 4/2008 | Jochelson et al. |
| 2010/0280402 A1 | 11/2010 | Dunbar et al. |
| 2011/0293195 A1 | 12/2011 | Nakagami et al. |
| 2014/0073960 A1 | 3/2014 | Rodriguez-Llorente et al. |
| 2014/0114147 A1 | 4/2014 | Romesburg |
| 2014/0213863 A1 | 7/2014 | Loseu et al. |
| 2014/0257049 A1 | 9/2014 | Soundarapandian et al. |
| 2015/0094552 A1 | 4/2015 | Golda et al. |
| 2015/0094592 A1 | 4/2015 | Ravindran et al. |
| 2015/0196256 A1 | 7/2015 | Venkatraman et al. |

(Continued)

FOREIGN PATENT DOCUMENTS

JP 2001340309 A 12/2001

OTHER PUBLICATIONS

Pande, Tarkesh; Magee, David Patrick, U.S. Appl. No. 15/203,859, filed Jul. 7, 2016 for "Heart Rate Estimation Apparatus Using Digital Automatic Gain Control," 32 pages.

(Continued)

*Primary Examiner* — Michael W Kahelin
(74) *Attorney, Agent, or Firm* — Michael A. Davis, Jr.; Charles A. Brill; Frank D. Cimino

(57) ABSTRACT

A photoplethysmogram system includes a plurality of sensors, each sensor capable of providing a sensor signal, and an adaptive filter capable of receiving a first input signal and computing an output. The photoplethysmogram system is capable of operating the filter in sequential stages, such that at each different stage the first input signal is a different sensor signal.

6 Claims, 4 Drawing Sheets

(56) References Cited

U.S. PATENT DOCUMENTS

| | | | |
|---|---|---|---|
| 2015/0196257 A1 | 7/2015 | Yousefi et al. | |
| 2015/0313549 A1* | 11/2015 | Lee | A61B 5/681 600/479 |
| 2015/0366469 A1 | 12/2015 | Harris et al. | |
| 2016/0317097 A1* | 11/2016 | Adams | A61B 5/721 |
| 2016/0324477 A1 | 11/2016 | Gunturi et al. | |
| 2017/0020398 A1 | 1/2017 | Emadzadeh | |

OTHER PUBLICATIONS

Pande, et al. U.S. Appl. No. 15/237,941, filed Aug. 16, 2016 for "Heart Rate Estimation Apparatus with State Sequence Optimization," 35 pages.

Hertzman, Alrick B., "The Blood Supply of Various Skin Areas as Estimated by the Photoelectric Plethysmograph," Department of Physiology, St. Louis University School of Medicine, Published Jul. 18, 1938; pp. 328-340.

Wijshoff, Ralph W. C. G. R.; Mischi, Massimo; Veen, Jeroen; Van Der Lee, Alexamder M.; Aarts, Ronald M., "Reducing Motion Artifacts in Photoplethysmograms by Using Relative Sensor Motion: Phantom Study," Journal of Biomedical Optics 17(11), 117007 (Nov. 2012), 16 pgs.

Fukushima, Hayato; Kawanaka, Haruki; Bhuiyan, MD. Shoaib; Oguri, Koji, "Estimating Heart Rate Using Wrist Type Photoplethysmography and Acceleration Sensor While Running," 34th Annual International Conference of the IEEE EMBS, San Diego, California, Aug. 28-Sep. 1, 2012, pp. 2901-2904.

Zhang, Zhilin; Pi, Zhouyue; Liu, Benyuan, "Troika: A General Framework for Heart Rate Monitoring Using Wrist-Type Photoplethysmographic Signals During Intensive Physical Exercise," IEEE Transactions on Biomedical Engineering, vol. 62, No. 2, Feb. 2015, 10 pgs.

Schack, Tim; Sledz, Christian; Muma, Michael; Zoubir, Abdelhak M., "A New Method for Heart Rate Monitoring During Physical Exercise Using Photoplethysmopraphic Signals," Signal Processing Group, Technische Universitat Darmstadt, Merckstr. 25, 64283 Darmstadt, Germany, 5 pgs.

Karantonis, Dean M.; Narayanan, Michael R.; Mathie, Merryn; Lovell, Nigel H.; Celler, Branko G., "Implementation of a Real-Time Human Movement Classifier Using a Triaxial Accelerometer for Ambulatory Monitoring," IEEE Transactions on Information Technology in Biomedicine, vol. 10, No. 1, Jan. 2006, pp. 156-167.

International Search Report for PCT/US2016/063780 dated Mar. 6, 2017 (2 pages).

Epifanio da Franca, et al; "Analog-to-Digital Conversion" Wiley Encyclopedia of Electrical and Electronics Engineering, edited by John G. Webster, published 2000 by John Wiley & Sons, Inc. 40 pages.

Allen, et al; "Photoplethysmography and its application in clinical physiological measurement"; Physiological Measurement, vol. 28, No. 3; 2007; 22 pages.

* cited by examiner

OPERATING A FILTER, BY A PHOTOPLETHYSMOGRAM SYSTEM, IN SEQUENTIAL STAGES, WHERE AN INPUT SIGNAL TO THE FILTER AT EACH DIFFERENT STAGE IS FROM A DIFFERENT SENSOR — 602

PHOTOPLETHYSMOGRAM WITH MOTION ARTIFACT COMPENSATION

BACKGROUND

A plethysmogram is a measurement of the volume of an organ. A photoplethysmogram (PPG) is a plethysmogram obtained using optics. One application of PPGs is heart rate monitoring. A source of light (typically a Light-Emitting-Diode (LED)) illuminates the skin and underlying tissue and a light-intensity sensor (typically a photo-diode) measures the amount of light either transmitted or reflected. The intensity of the transmitted or reflected light corresponds to the amount of blood volume. With each cardiac cycle, the blood volume changes in the arteries and arterioles in the subcutaneous tissue, and changes in blood volume modulate the transmitted or reflected light.

One common PPG application is heart-rate monitoring during physical activity or continuous health monitoring during daily life. Wrist-bands, watches, and other wearable heart-rate monitors using PPG sensors are commonly available. One problem with wearable heart-rate monitors is that the PPG signal is also modulated by motion artifacts due to arm movement, walking, jogging, etc. Motion can move the PPG sensor relative to the skin, or change the contact force, or deform the tissue next to the sensor, or affect blood flow near the sensor (for example by partially occluding an artery), each of which may affect the PPG signal.

Reduction of motion-induced artifacts in PPG signals has been extensively investigated in industry and academia. Most approaches use accelerometers to separately measure motion. One approach uses accelerometer signals to control various types of adaptive filters. Other approaches require real-time computation of three Fast-Fourier-Transforms (FFT's) to determine three-dimensional motion frequency, which leads to high complexity, expense, and increased battery drainage.

DETAILED DESCRIPTION

Figure 1:
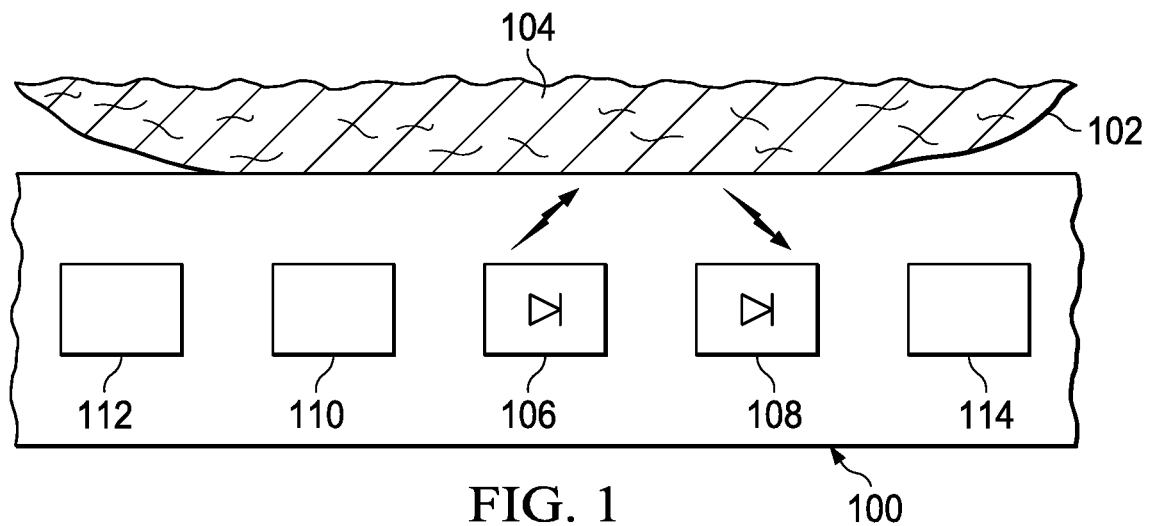
FIG. 1 is a cross-section block diagram of an example embodiment of a PPG system.

FIG. 1 illustrates an example PPG system 100 adjacent to skin 102 and underlying tissue 104. The PPG system 100 may be, for example, part of a wrist band or wrist watch, or may be part of an apparatus attached to another part of the body such as an earlobe, forehead, or ankle. The PPG system 100 includes a light emitter 106 and a light detector 108 for measuring heart rate (derived from measuring blood volume) in the tissue 104. The PPG system 100 may also include, for example, an accelerometer 110, which may have multiple sensors for multiple dimensions. The PPG system 100 may also include one or more additional sensors 112 for measuring relative motion between the PPG sensor 106 and the skin 102, or tightness of the PPG 100 against the skin 102, or other sensors. The PPG system 100 may also include a processor (or controller, or digital signal processor, or ASIC, etc.) 114 for processing signals from the sensors (108, 110, 112) to derive a heart-rate with reduced noise artifacts. Alternatively, the sensor signals may be processed externally, for example, by a cell phone or fitness monitor.

The processor 114 includes an adaptive digital filter (not illustrated in FIG. 1), which is used to reduce motion artifacts from the PPG signal. Examples of suitable filters include the Normalized Least Mean Squares Filter (NLMS) and Recursive Least Squares Filter (RLS). In the following discussion, the adaptive digital filter is operated sequentially in a daisy-chain fashion. At each stage, motion artifacts are removed from the PPG signal. As will be discussed in more detail below, sequential operation of the adaptive digital filter enables the system 100 to advantageously use more sensor signals than just raw accelerometer signals to reduce motion artifacts, enables an adaptive digital filter parameter to be optimized for each type of sensor, and enables using only one FFT computation for each heart-rate update.

Figure 2A:
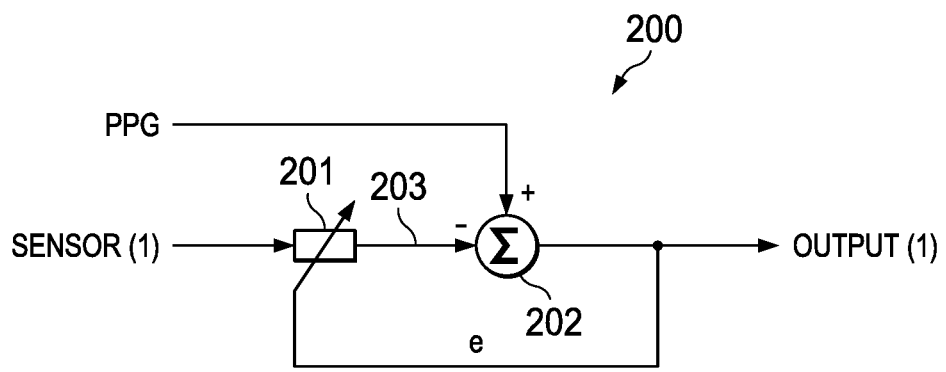
FIG. 2A is a block diagram schematic of an adaptive filter during a first stage of sequential operation.
Figure 2B:
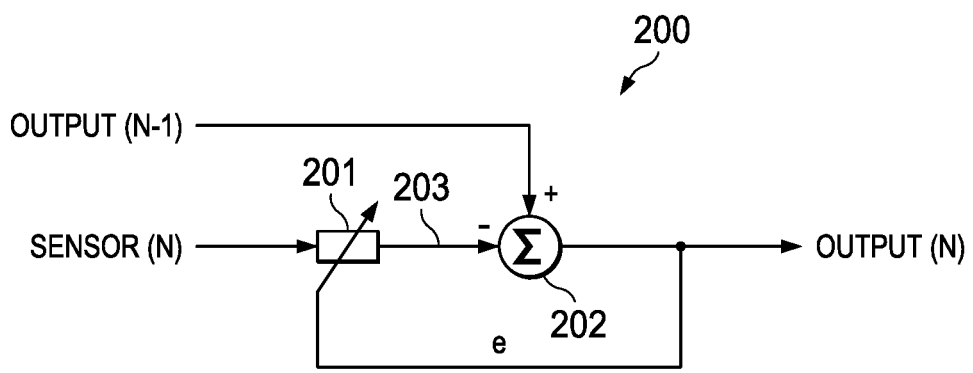
FIG. 2B is a block diagram of the adaptive filter of FIG. 2A during later stages of sequential operation.

FIGS. 2A and 2B illustrate an adaptive digital filter 200 being operated sequentially in a daisy-chain fashion. FIG. 2A illustrates the signals during the first stage of the operation. PPG is the signal from the optical PPG sensor. SENSOR(1) is a signal from a first sensor used for artifact mitigation, which may be, for example, one dimension output of a three-dimensional accelerometer, or may be a signal from a sensor for relative motion between the PPG sensor and the skin, or a signal from some other artifact mitigation sensor. In FIG. 2A, the adaptive digital filter 200 receives the signal SENSOR(1) from the first sensor, an estimation filter 201 digitally computes an estimation signal 203, and at a summing junction 202, the estimation signal 203 is subtracted from the PPG signal. The resulting difference e is fed back to the estimation filter 201 and the estimation filter 201 iteratively adapts by adjusting filter parameters to reduce e. At the end of the iteration process the resulting output of the summing junction (OUTPUT(1)) is the PPG signal with motion artifacts measured by the first sensor (SENSOR(1)) reduced.

In FIG. 2B, for stages after the first stage, the adaptive digital filter 200 receives a signal SENSOR(N) from the Nth sensor, the estimation filter 201 digitally computes an estimation signal 203, and at the summing junction 202 the estimation signal 203 is subtracted from the filter output signal (OUTPUT(N−1)) from the previous stage. As a result, at each stage, additional noise artifacts are reduced.

Figure 3:
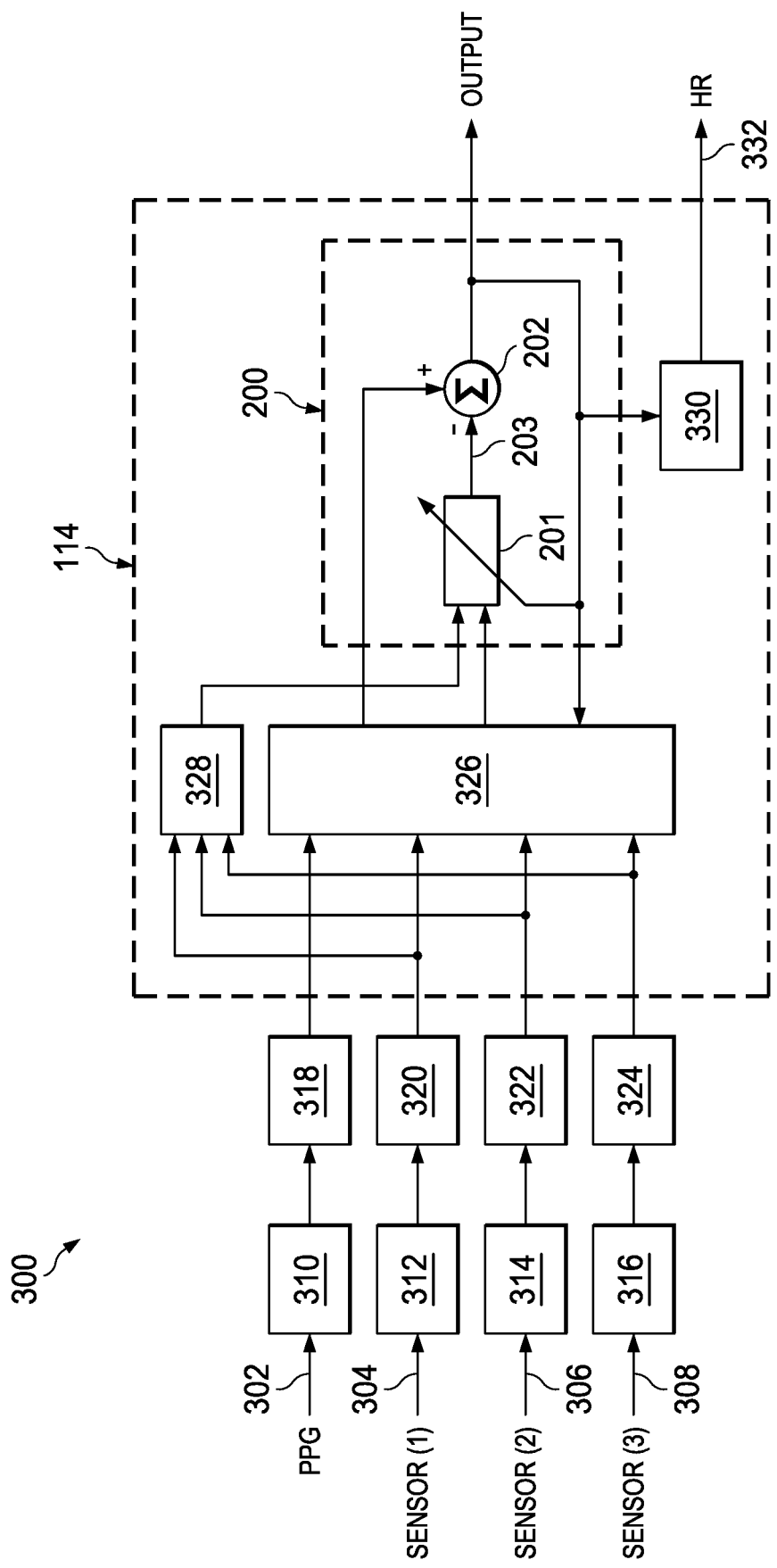
FIG. 3 is a block diagram schematic of an example embodiment of a system for processing PPG sensor signals.

FIG. 3 illustrates an example embodiment of an improved photoplethysmogram system 300. In FIG. 3, the system receives four sensor signals (302, 304, 306, 308). In the example of FIG. 3, the first signal 302 is the output of the PPG sensor and signals 304-308 are the outputs of accelerometer sensors. The sensor signals (302-308) are band-pass filtered (310, 312, 314, 316) and simultaneously digitized by Analog-to-Digital Converters (ADCs) (318, 320, 322, 324). The resulting digital signals are received by a processor (or controller, or digital signal processor, or ASIC) 114 (as illustrated in FIG. 1) and stored in processor memory 326. The processor 114 includes an adaptive digital filter 200 (as illustrated in FIGS. 2A and 2B). The processor memory 326 stores the digitized signals and the output of the adaptive digital filter 200. The processor 114 also includes a stationary detector 328 and a FFT function 330. The digital adaptive filter 200 (including the estimation filter 201 and the summing junction 202), stationary detector 328, and FFT 330 may all be implemented by software.

In the example system 300, the adaptive digital filter 200 operates sequentially in stages as illustrated in FIGS. 2A and 2B. During the first stage, the inputs to the adaptive digital filter 200 are the stored first accelerometer signal 304 and the stored PPG sensor signal 302. The resulting filter output (OUTPUT(1)) is stored in memory 326. During the second stage, the inputs to the adaptive digital filter 200 are the second accelerometer signal 306 and the stored output from the first stage (OUTPUT(1)). During the third and final stage, the inputs to the adaptive digital filter 200 are the third accelerometer signal 306 and the stored output from the second stage (OUTPUT(2)). An FFT 330 is computed for the output from the final stage (OUTPUT(3)) of the adaptive digital filter 200 and the peak frequency in the FFT output is the estimated heart rate 332.

In the example of FIG. 3 the only sensor signals are the PPG sensor signal 302 and accelerometer signals (304-308). However, one advantage of sequential operation of the adaptive digital filter 200 is that additional sensor signals can easily be added. Measurements of particular interest include (1) measurement of relative motion between the PPG sensor and the skin and (2) measurement of how tightly or loosely the PPG sensor is attached. In general, tightness is a DC measurement and relative motion is an AC measurement. The same sensor may be used for both. For example, a separate light source (for example a laser diode) with a wavelength optimized for detecting tissue instead of blood volume may be used to detect tightness and/or motion between the PPG sensor and the skin. Alternatively, conductive sensors of the type used to sense electroencephalograms (EEGs) or electrocardiograms (EKGs) may be used to detect resistance through the connection to the skin, or capacitance between the sensor and the skin, to measure tightness and/or relative motion between the PPG sensor and the skin. Alternatively, sequential operation of the adaptive digital filter 200 can accommodate signals from sensors outside the PPG apparatus (for example, sensors mounted on an ankle or in an insole for detecting leg motion and/or foot impact, or inertial sensors in a cell phone).

If, for example, the adaptive digital filter 200 is a NLMS filter, for each iteration n+1, the estimation signal 203 is $h(n+1)=h(n)+\mu(x(n)e(n))$, where $x(n)$ is the input, $e(n)$ is the output and feedback signal from the summing junction 202 (see FIGS. 2A and 2B), and $\mu$ is the step size (or adaptation constant). Operating the adaptive digital filter 200 sequentially in stages enables the PPG system to optimize the value of the step size $\mu$ to maximize convergence speed of the adaptive digital filter 200 at each stage depending on the type of sensor signal, and/or depending on the output of a loose/tight sensor, and/or depending on whether there is motion.

Figure 4:
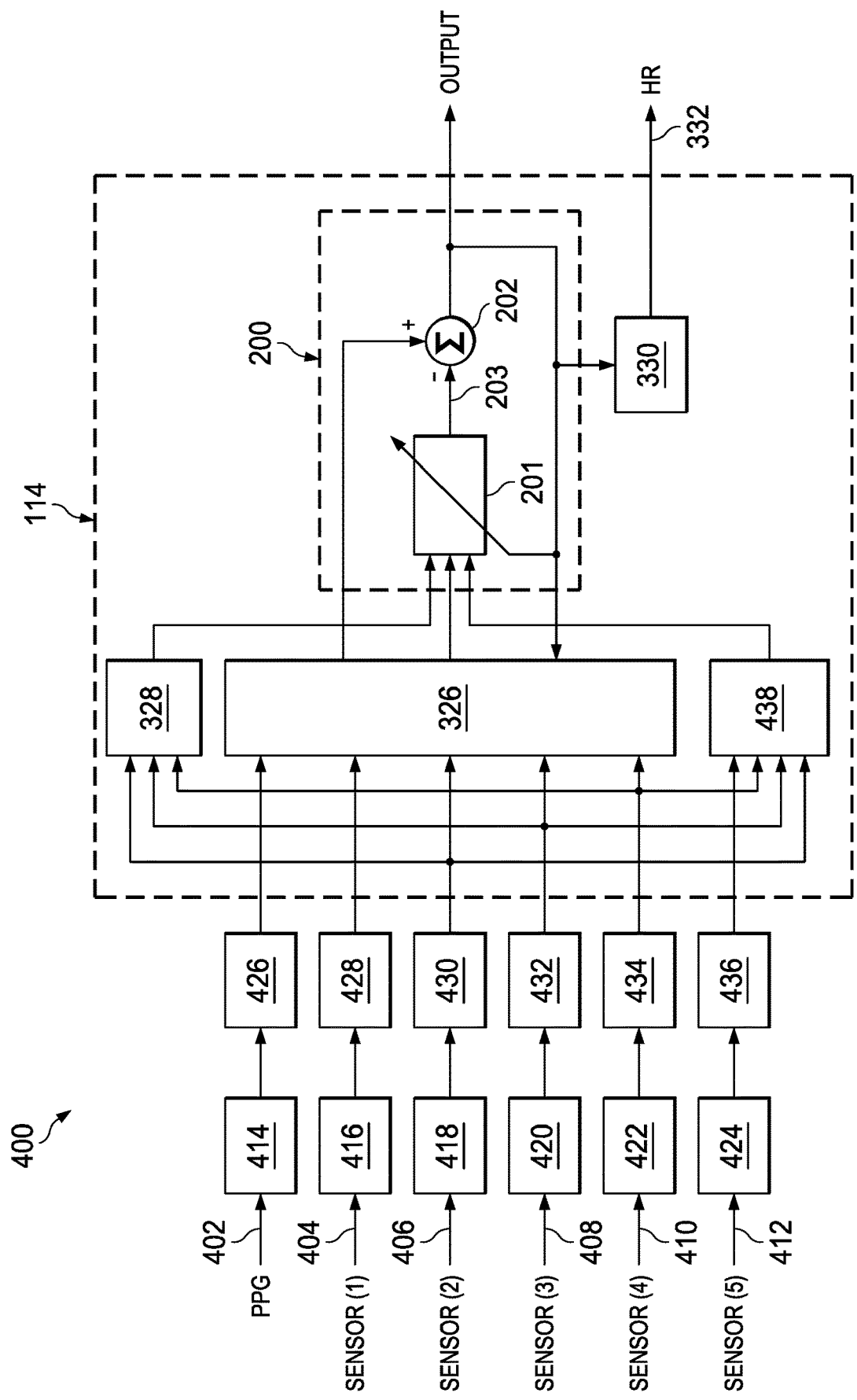
FIG. 4 is a block diagram schematic of an alternative example embodiment of a system for processing PPG signals.

FIG. 4 illustrates an alternative example embodiment of a photoplethysmogram system 400. Sensor signals (402-412) are filtered by band pass filters (414-424) and digitized by ADC's (426-436). The resulting digital signals are received by a processor (or controller, or digital signal processor, or ASIC) 114 and stored in processor memory 326. The example system 400 includes a sensor signal (SENSOR(1)) (which may be for example, a signal from a sensor for measuring relative motion between the PPG sensor and the skin) in addition to signals from three accelerometer sensors (SENSOR(2), SENSOR(3), SENSOR(4)), all of which are used by the adaptive digital filter 200. In addition, the system 400 includes a tightness sensor (SENSOR(5)). Signals from the accelerometer sensors (SENSOR(2), (SENSOR(3), SENSOR(4)) and the signal from the tightness sensor (SENSOR(5)) are used to vary the filter step size p.

The system 400 includes a stationary detector 328 and a FFT function 330 (as in FIG. 3). The system 400 also includes a step-size estimator 438 that receives the signal from the tightness sensor (SENSOR(5)) and the three accelerometer signals (SENSOR(2), (SENSOR(3), SENSOR(4)) and determines the step size $\mu$ for the estimation filter 201. The value of $\mu$ is dependent on tightness and on which sensor signal is being filtered. The following table provides example values of $\mu$ depending on tightness and sensor signal. The values in the table assume that SENSOR(1) is a signal from sensor for measuring relative motion between the PPG sensor and skin and that the remaining signals are from accelerometer sensors. If the fit is loose then relative motion between the PPG sensor and the flesh may contribute more to motion artifacts than body motion as measured by an accelerometer. If the fit is tight then body motion may dominate motion artifacts.

| SENSOR | $\mu$ (loose fit) | $\mu$ (tight fit) |
|---|---|---|
| SENSOR(1) | 0.1 | 0.025 |
| SENSOR(2) | 0.025 | 0.1 |
| SENSOR(3) | 0.025 | 0.1 |
| SENSOR(4) | 0.025 | 0.1 |

In the embodiment of FIG. 3, the stationary detector 328 receives all three digitized accelerometer signals (304-308) and determines whether there is any motion. In the embodiment of FIG. 3, if there is no motion, then filter stages two and three for the adaptive digital filter 200 are not necessary and the FFT 330 can be computed on the output of the first stage. Likewise, if there is no motion in any one dimension, then the corresponding filter stage can be omitted. For example, if sensor signal 304 is quiet, then the first stage of the adaptive digital filter 200 can use the second stored sensor signal 306, and so forth. Likewise, in the embodiment of FIG. 4, the stationary detector 328 receives all three digitized accelerometer signals (406-410) and determines whether there is any motion. If there is no motion, then filter stages two, three, and four for the accelerometer signals (406-410) are not necessary and may be omitted, and if there is no motion in any one dimension, then the corresponding stage can be omitted.

Figures 5, 6:
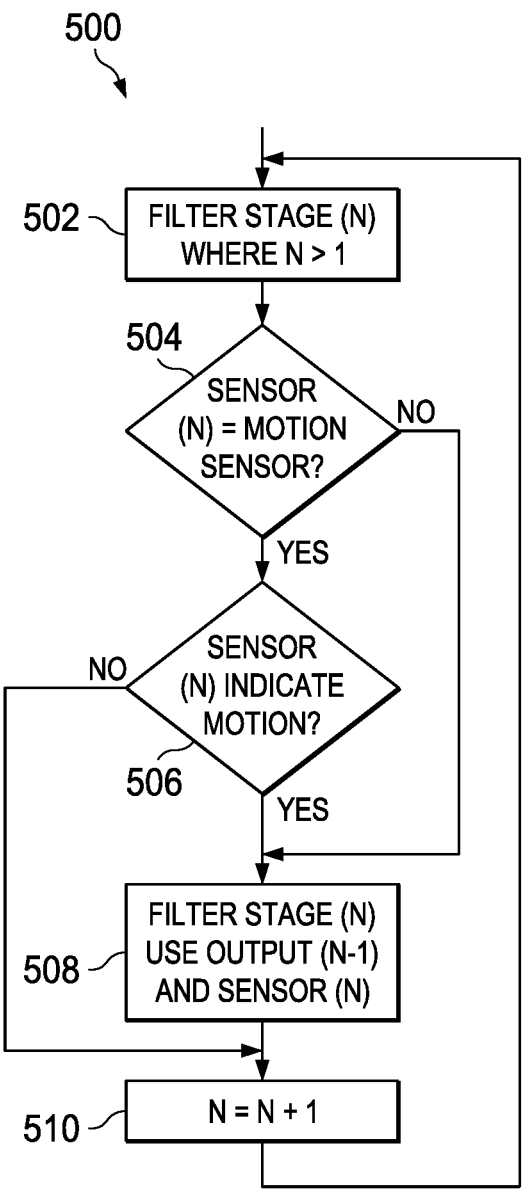
FIG. 5 is a flow chart of an example embodiment of a method to omit filter stages when there is no motion in at least one dimension.
FIG. 6 is a flow chart of an example embodiment of a method for processing PPG sensor signals.

FIG. 5 is a flow chart illustrating a method 500 to omit filter stages when there is no motion in at least one dimension. At step 502, the adaptive digital filter 200 is at stage (N) where N is greater than one. At step 504, if sensor (N) is a motion sensor, and if at step 506 there is no motion indicated by sensor (N), then filter stage (N) is omitted and the process proceeds to step 510 where N is incremented. At step 504, if sensor (N) is not a motion sensor, or if at step 506 sensor (N) is a motion sensor and motion is detected, then the process proceeds to step 508 where filter stage (N) is computed using the output from sensor stage (N−1) and the stored signal from sensor (N).

FIG. 6 illustrates an example embodiment of a method 600 for controlling a photoplethysmogram system. At step 602 a photoplethysmogram system operates a filter in sequential stages, where an input signal to the filter at each different stage is from a different sensor.

While illustrative and presently preferred embodiments of the invention have been described in detail herein, it is to be understood that the inventive concepts may be otherwise variously embodied and employed and that the appended claims are intended to be construed to include such variations except insofar as limited by the prior art.

What is claimed is:

1. A photoplethysmogram system, comprising:
a photoplethysmogram device including N sensors adapted to be placed in proximity to tissue of a wearer of the photoplethysmogram device, where N is an integer number greater than two, the N sensors having respective N sensor outputs, and the N sensors including: a photosensor having a photosensor output; and a motion sensor having a motion output;
an adaptive filter configured to generate an output signal indicative of a heart rate of the wearer, the adaptive filter configured to operate in N sequential stages, each of the N sequential stages having a respective stage output and respective first and second inputs, and the N sequential stages including:
a first stage whose first input is coupled to a first one of the N sensor outputs, and whose second input is coupled to the photosensor output; and
nth stages, where n is an integer number ranging from 2 through N, in which: the first input of the nth stage is coupled to an nth one of the N sensor outputs; and the second input of the nth stage is coupled to the stage output of the (n−1)th stage; and
a stationary detector coupled to the motion output and configured to detect motion responsive to a motion signal at the motion output, in which at least one of the N sequential stages is bypassable responsive to the detected motion being absent in at least one dimension.

2. The photoplethysmogram system of claim 1, wherein the photosensor is configured to receive light reflected from the tissue of the wearer, and the adaptive filter includes for each of the N sequential stages:
an estimation filter having a filter input and an estimation output, the filter input coupled to the stage's first input; and
a summing junction having a difference output and first and second junction inputs, the first junction input coupled to the estimation output, the second junction input coupled to the stage's second input, and the summing junction configured to sum a signal at the estimation output with a signal at the stage's second input to form a difference signal at the difference output, in which parameters of the adaptive filter are adjustable to minimize the difference signal.

3. The photoplethysmogram system of claim 1, wherein the photoplethysmogram system is configured to measure the heart rate by computing a fast Fourier transform (FFT) responsive to the stage output of the Nth stage.

4. The photoplethysmogram system of claim 1, wherein the adaptive filter is a programmed processor.

5. The photoplethysmogram system of claim 1, wherein the adaptive filter is an application-specific integrated circuit.

6. The photoplethysmogram system of claim 1, wherein the adaptive filter is configured to use a different step size for each of the N sequential stages responsive to which one of the sensor outputs is coupled to the stage's first input.

* * * * *